United States Patent [19]

Wasserman

[11] Patent Number: 4,611,583

[45] Date of Patent: Sep. 16, 1986

[54] SACCADIC ENHANCER APPARATUS

[76] Inventor: Jacob Wasserman, 24 Phyllis Dr., Pomona, N.Y. 10970

[21] Appl. No.: 702,677

[22] Filed: Feb. 19, 1985

[51] Int. Cl.[4] .......................... A61H 5/00; A61B 3/00

[52] U.S. Cl. .................................... 128/76.5; 351/203

[58] Field of Search .................... 128/76.5, 745, 25 A; 351/203

[56] References Cited

U.S. PATENT DOCUMENTS

| | | | |
|---|---|---|---|
| 686,616 | 11/1901 | Johnquest | 128/76.5 |
| 1,043,981 | 11/1912 | Strong | 128/76.5 |
| 1,201,841 | 10/1916 | Mahieu | 128/76.5 |
| 2,476,708 | 7/1949 | Day | 128/76.5 |
| 3,172,404 | 3/1965 | Copenhaver | 128/76.5 |

FOREIGN PATENT DOCUMENTS

| | | | |
|---|---|---|---|
| 589748 | 6/1947 | United Kingdom | 128/76.5 |

*Primary Examiner*—Clifford D. Crowder

*Attorney, Agent, or Firm*—Arthur L. Plevy

[57] ABSTRACT

A saccadic enhancer apparatus which will operate to improve and develop accurate saccadic fixation for a user by providing horizontal, vertical, oblique and circular patterns for the user to observe. The enhancer employs a timing generator which produces a plurality of selectable time periods during which period a particular selected pattern will be provided. The patterns selected are implemented by a plurality of LED devices which are arranged on a display screen according to the patterns desired. The pattern to be implemented is selected by a selector switch and in the case of a horizontal line pattern the LED display operates from left to right and from right to left for the selected time period. When the circular mode is selected a circular pattern is provided which moves in a clockwise or counter clockwise direction and at the end of a complete scan, a smaller circular pattern is switched to. The switching between the larger diameter pattern and the small diameter pattern is automatically accommodated by the apparatus.

10 Claims, 5 Drawing Figures

SACCADIC ENHANCER APPARATUS

THE BACKGROUND OF THE INVENTION

This invention relates to apparatus for exercising the eyes and more particularly to such apparatus for developing an accurate saccadic fixation in horizontal, vertical, oblique and circular directions.

The prior art is replete with a number of patents which depict various exercising devices to enable a patient to exercise the eye muscles in a beneficial way.

U.S. Pat. No. 2,588,191 entitled CONTROL UNITS FOR VISUAL TRAINING DEVICES, issued on Mar. 4, 1952 to M. Zuras shows a visual training device which consists of a series of light bulbs which are energized individually or simultaneously in various sequences. The device is relatively complicated in structure and is extremely difficult to use and to manufacture.

U.S. Pat. No. 2,718,227 entitled VISUAL EXERCISING DEVICES by A. Powell, issued on Sept. 20, 1955 shows a visual exercising device which produces patterns by the use of light bulbs and allows a user to view the displayed patterns for visual training purposes. The device is also a relatively complicated device.

There are, of course, many other patents which show other vision therapy devices which are implemented to allow a handicapped user to exercise various muscles in order to achieve better control. In any event, certain individuals suffer from eye muscle defects which cause them extreme problems in muscle control and response time to movement. This is due to the fact that such persons cannot move their eyes in the required directions as in the horizontal, vertical, oblique and circular directions.

In order to improve this disability, these people have to be trained to increase their eye scanning in all directions in order to enable them to function properly. In conjunction with the above problem, such a training device should also offer the physician or practitioner the ability to monitor a handicapped individual's disabilities and to thereby enable the practitioner to further assist the individual in overcoming the disability. In this manner, the exercising device can help the practitioner to establish the nature of the difficulties and to, therefore, enable the patient to develop directional and laterability skills as well as spatial awareness. Hence, in order to overcome these problems, the saccadic enhancer according to this invention can be used by the practitioner as well as patients to enable the patient to increase the strength of their eye muscles and response time to movement as well as to enable the practitioner to determine the extent and nature of the disabilities.

It is, therefore, an object of the present invention to provide an improved eye exercising apparatus which aparatusl is capable of generating a plurality of patterns in the form of sequential light movements and which patterns can be varied in direction and speed according to the particular disability of the handicapped person.

BRIEF DESCRIPTION OF THE PREFERRED EMBODIMENT

A saccadic enhancer apparatus for training a user to develop accurate saccadic fixation in a plurality of directions, comprising a display panel having positioned thereon a plurality of light emitting devices with a first plurality of devices arranged in a circular pattern and with a second plurality of said devices arranged in a horizontal line pattern along a first diameter of said circular pattern, and a third plurality of said devices arranged in a vertical line pattern along a second diameter of said circular pattern transverse to said first diameter, first selectable logic means coupled to said first plurality of devices to activate said devices in a sequential mode to cause respective devices in said plurality to illuminate to provide a circular pattern of illumination, second selectable logic means coupled to said second and third plurality of devices to cause either of said devices in said second and third plurality of devices to activate to provide said horizontal or vertical line patterns in a sequential mode selection means for selecting said first or second logic means to cause said circular or linear pattern to be displayed and selectable timing means operative when selected to enable said selected mode to be displayed for a period determined by said timing means.

DETAILED DESCRIPTION OF THE PREFERRED EMBODIMENT

Figure 1:
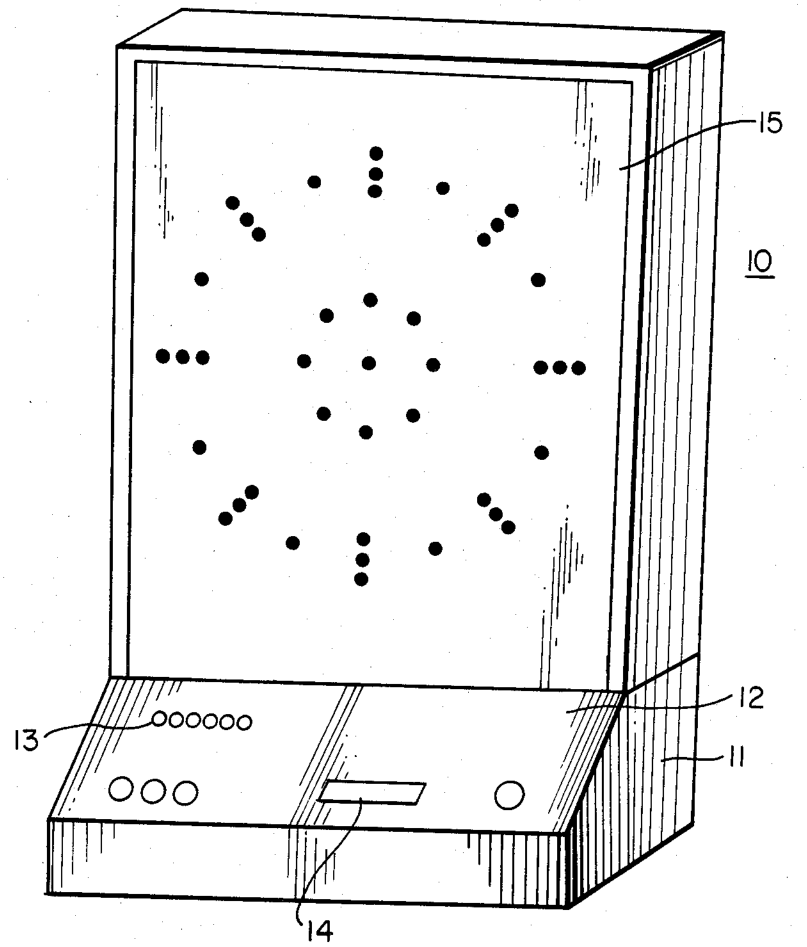
FIG. 1 is a perspective plan view of a saccadic enhancer according to this invention.

Referring to FIG. 1, there is shown a perspective plan view of a saccadic enhancer 10 according to this invention.

As seen in FIG. 1, the enchancer 10 comprises a housing having a bottom portion 11 with a sloping front panel 12 upon which is positioned various control and selection switches as 13 and 14, to be explained, and in order to control operation and the sequencing of the light display panel 15.

As can be seen, the display panel 15 contains a plurality of LED devices which are arranged to allow the associated control circuitry to sequence the LED devices to provide linear and circular patterns to enable a user to exercise his eyes while enabling a practitioner to observe the user and his responses. Thus the enhancer 10 is capable of providing light displays which operate in horizontal, vertical, oblique and circular directions. The display is controlled so linear patterns move from left to right and from right to left and soon in the horizontal, vertical and oblique directions, while circular patterns move clockwise or counter clockwise and alternate between a large diameter and a small diameter circle.

Figure 2:
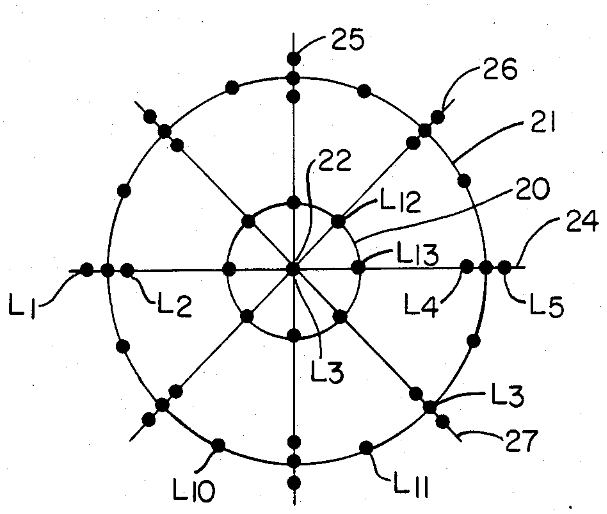
FIG. 2 is a diagram showing the various patterns which can be generated by the enhancer of FIG. 1.

Referring to FIG. 2, a graphic representation of the display panel 15 is given. As one can see, the LED format manifests two concentric circles 20 and 21, both of which are arranged about the center LED 22. A series of linear patterns such as a horizontal pattern indicated by line 24, a vertical pattern indicated by line 25, and oblique patterns at 45 and 135 degree angles indicated by lines 26 and 27 are provided and controlled as well.

The speed of motion of the various light patterns can be controlled by varying the operating rate as well as direction. In this manner, the user can exercise his eyes and muscles in all directions. The various LED's can be employed in red or green colors to enable a user to wear red or green glasses. This mode of operation allows antisuppression therapy to help improve binocularity.

The circular patterns enable the patient to enhance pursuit fixation to help improve rotations and versions. In regard to amblyopia, the use of red glasses enables a practitioner to view the patients suppressions and further enable the stimulation of the amblyopic eye. The right to left movement of the horizontal line patterns or the up and down movement of the vertical patterns helps in the establishment of directionality and laterability skills as well as spatial awareness.

One can use the enhancer 10 to train athletes as well as the visually handicapped to enable them to fixate more accurately and improve peripheral visual skills. Essentially, the enhancer 10 will help to improve and develop an accurate saccadic fixation in horizontal, vertical, oblique and circular directions. The enhancer 10 teaches and trains for rapid eye scanning in all pertinent directions. The use of variable speed displays allows the patient's or user's eye movement to be monitored by the practitioner to further determine the nature and extent of the problems.

As will be explained, the patterns generated are electronically controlled and operation and control of the patterns is rendered by access to the controls on panel 12 of the enhancer 10.

The enhancer 10 contains control on the front panel 12 to enable the user to change the pattern as from a circular to a linear pattern and to also change the timing interval that the pattern is activated for. In this manner, both the user and the practitioner can implement a given pattern for a given time duration. The time selected can be changed by means of controls on panel 12 as well as the repetition rate of the pattern can be varied as will be further explained.

Figure 3:
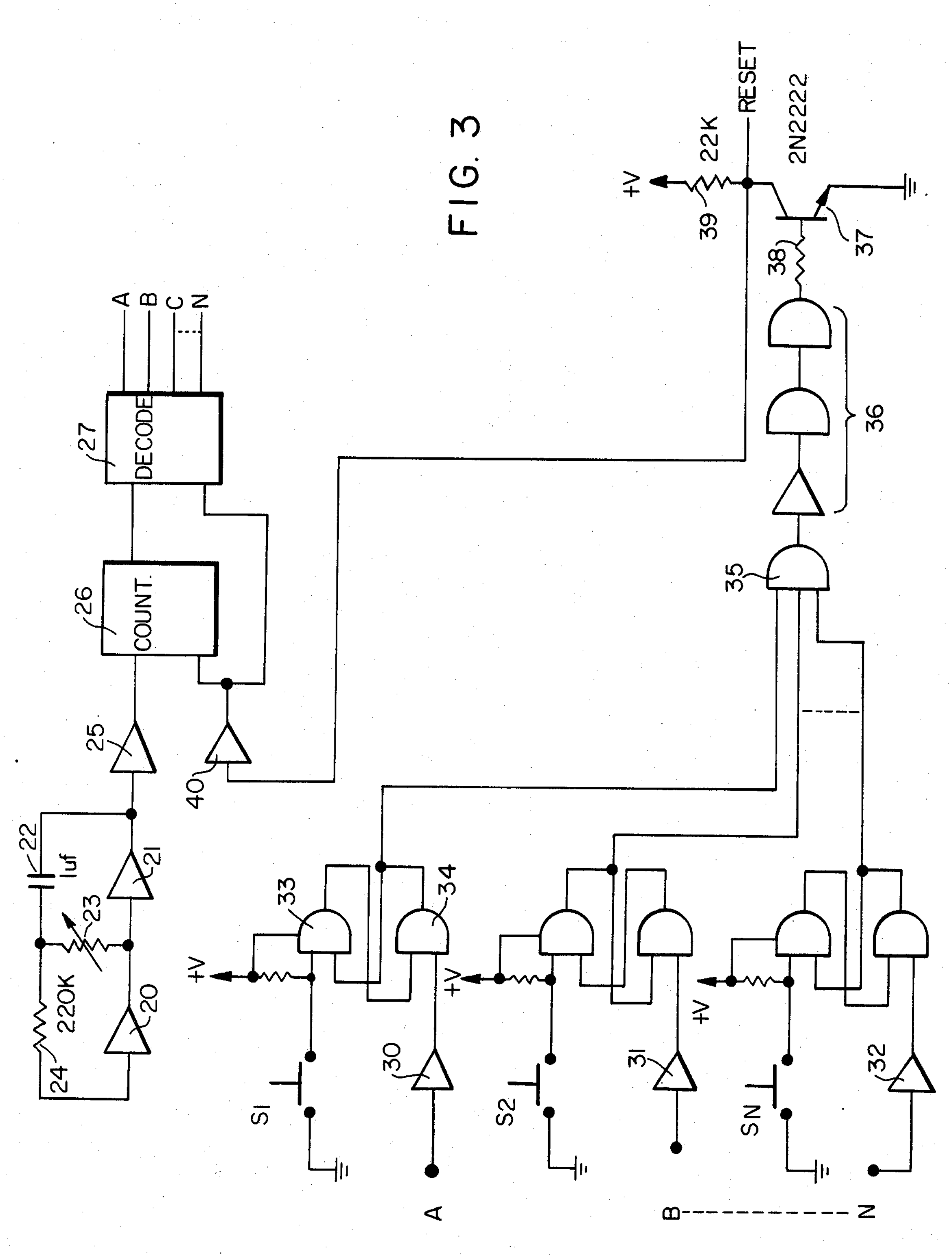
FIG. 3 is a circuit diagram showing the timing control for the enhancer.

Referring to FIG. 3, there is shown a timer circuit which is employed in this invention.

A low frequency clock signal or timing signal is generated by means of the circuit consisting of inverters 20 and 21 which are arranged in a feedback loop with capacitor 22 and variable resistor 23 functioning to control the timing rate of the output pulses. The resistor is a feedback resistor which appears between the input and output of amplifier 20. The circuit configuration including the inverters 20 and 21 is well known. The output clock signal is coupled via an inverter 25 to the input of a counter and decoder circuits 26 and 27.

The counter 26 is a conventional binary counter and many examples of which can be purchased as commercial integrated circuits as is the decoder 27. The counter 26 operates to divide the input clock signal from inverter 25 by a factor of eight and the decoder decodes each of the eight states designated as A to N to produce timed outputs according to the state of the counter. The outputs of the decoder circuit 27 are applied to the inputs of a series of inverters as 30, 31, and 32. Each inverter is associated with a separate latch circuit. The latch circuits as seen in the Figure each consist of two AND gates as 33 and 34 having their outputs coupled to the input of the associated gate. This is a typical latch circuit configuration and is well known in the state of the art.

Each latch circuit is associated with a separate switch as S1, S2 and SN. The switches are momentary throw switches and for example are those switches shown in FIG. 1 as switch bank 13. In typical operation, there are six switches such as S1 to SN which are associated with six separate latch circuits. The output of each latch circuit is coupled to the input of an AND gate 35 whose output is inverted through inverters 36 and thereafter coupled to the base electrode of a transistor 37 via a current limiting resistor 38. The collector of the transistor is coupled through a collector resistance 39 to a source of operating potential as will be explained. The collector of transistor 39 provides a reset for the display circuitry.

The reset is also applied via inverter 40 to the counter 26 and the decode circuit 27. As indicated, there are six latch circuits and hence there are six switches S1 to SN. A typical timing operation is as follows for the latch employing gates 33 and 34. Initially, the output of the latch is high and all inputs to transistor 37 are high thereby indicating that transistor 37 is in the on state with the collector voltage being approximately at ground.

The output of inverter 40 is high and operates to reset the counter 26 and the decoder 27. When the push button S1 is activated, the output pin of gate 33 will go low and transistor 37 turns off. This will cause the inverter 40 to change states to thereby allow the counter 26 and decoder 27 to operate. When the A input from decoder 27 goes high, the latch circuit is reset via the inverter 30 and transistor 37 is turned on. This condition resets the counter and decoder. Hence when the reset signal at the collector of transistor 37 is high, the LED displays which were implemented by the enhancer 10 will operate as will be explained. When the reset signal is low, the displays are inhibited from operation.

Figure 4:
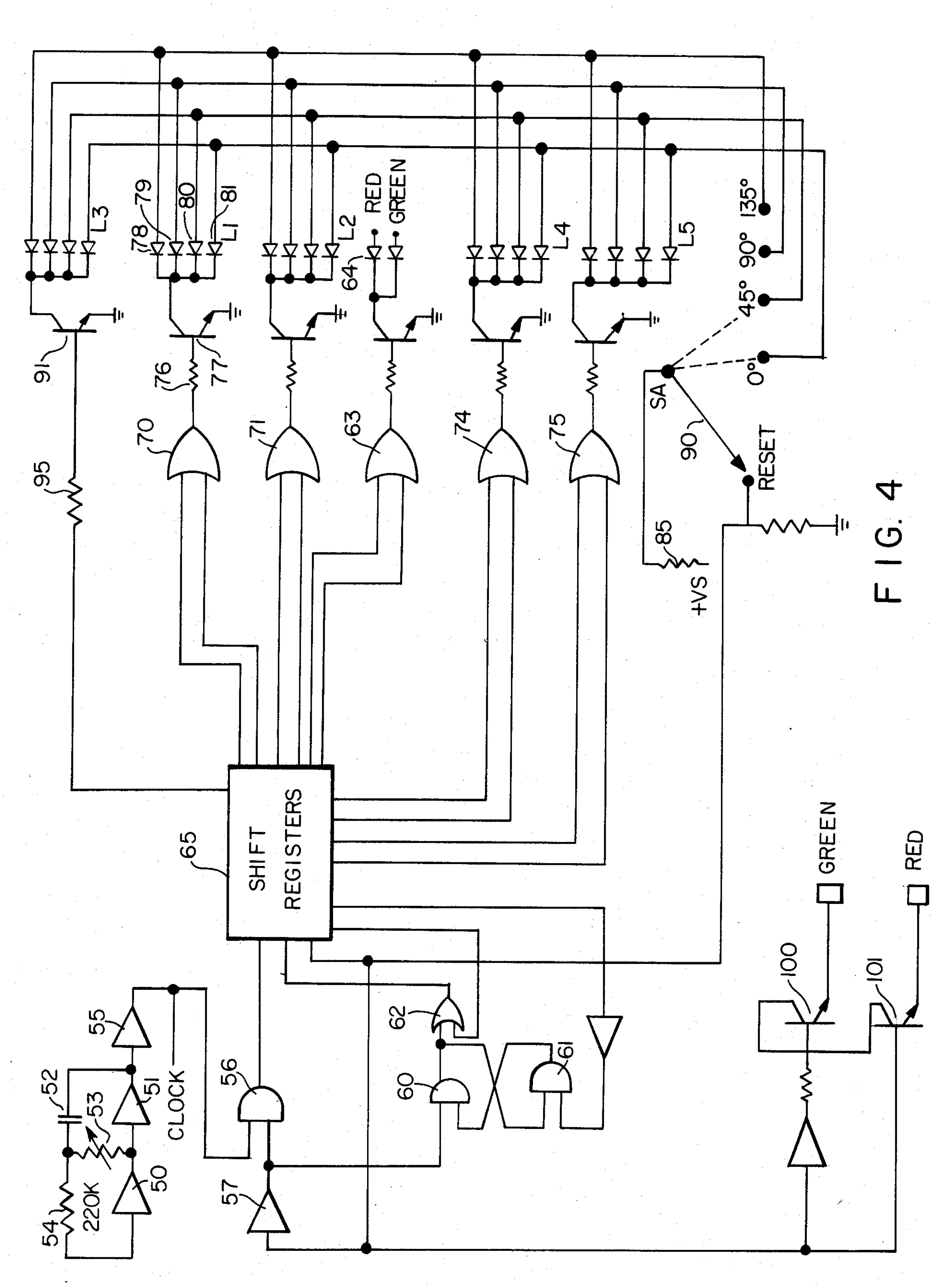
FIG. 4 is a circuit diagram showing the circuitry necessary for producing vertical, horizontal and oblique line patterns.

Referring to FIG. 4, there is shown the circuitry necessary to produce linear patterns via the LED displays as shown in FIGS. 1 and 2. The circuitry shown in FIG. 4 can produce a vertical or a horizontal line pattern as indicated in FIG. 2 by lines 24 and 25 and can also produce the oblique patterns as indicated in FIG. 2 by lines 26 and 27. Essentially, the circuit shown in FIG. 4 is driven by a separate clock which consists of inverters 50 and 51 arranged in a feedback loop with capacitor 52, resistor 53 and resistor 54. The clock circuit is of the same configuration as the timing clock shown in FIG. 2 but operates at a higher rate. The resistor 53 is a variable resistor to enable one to change the speed of operation or sequence speed and the control for altering the resistance of resistor 53 is also on the front panel 19 of the enhancer 10.

The output clock signal from inverter 51 is applied via an inverter 55 to the input of an AND gate 56. This signal passes through gate 56 when the system reset or the reset of FIG. 3 is low. As one can see, the rest of FIG. 3 is coupled to the input of an inverter 57 which has its output coupled to the input of the AND gate 56. When the rest is high, the inverter blocks the clock signal from passing through gate 56, while also setting a latch circuit consisting of gates 60 and 61. The output of the latch circuit is coupled via an OR gate 62 which sets the shift register so that OR gate 63 is operated to activate the LED 64 which is the red LED.

As seen from FIG. 4, the output of the AND gate 56 is coupled to the clock input of a shift register 65. The shift register 65 operates in a normal manner and essentially produces a series of sequential pulses which as seen from FIG. 4 are coupled to various OR gates as gates 70, 71, 63, 74, and 75. Each gate has its output coupled via a current limiting resistor as resistor 76 to the base electrode of an associated transistor as transistor 77. The collector electrode of a typical transistor as transistor 77 is coupled to four LED diodes as 78, 79, 80 and 81. Each diode has its anode coupled to a separate terminal designated as terminal 0 degrees, 45 degrees, 90 degrees and 135 degrees. In this manner and as will be explained, when switch SA is set to any position such as 0, 45, 90 or 135 degrees a voltage is applied to the anode of the selected diodes. These diodes are arranged as shown in FIG. 2 to provide the linear patterns as the horizontal line pattern for 0 degrees, the vertical line pattern for 90 degrees and the oblique line pattern for 45 degrees and 135 degrees.

Hence subsequent clock pulses will cause the shift register to shift through it various states and depending upon the setting of switch 90 which is the SA switch, the selected pattern will be illuminated at a rate depending upon the setting of the clock resistor 53. The switch SA or 90 is also on the front panel 19 of the enhancer 10. Thus as one can see from FIG. 4, the user sets switch 90 to the position desired such as to implement a horizontal, a vertical or an oblique display. The shift register 65 proceeds to alter states as a function of the clock signal and hence illuminate the appropriate LEDS which are coupled to the collector electrodes of the various transistors such as transistor 77 for example.

The resistor 85 which is coupled to the contact arm of switch 90 determines the operating current for each LED. The displays will operate until transistor 37 of FIG. 3 produce the reset signal which will then cause display operation to cease. In any event, one can also reset the display by moving switch SA to the reset position as shown at this position the line generator circuitry of FIG. 4 is disabled and hence the unit provides circular patterns as will be explained. It is noted that the top transistor 91 in FIG. 4 has its base electyrode directly coupled to the output of the shift register via a limiting resistor 95 and has its collector electrode coupled to the cathodes of four LED devices. The reason for this is as follows.

As one can see from FIG. 2, the center LED 22 is common to all linear displays. The display operates so that each line pattern is traversed in a first direction and then back again from that direction. Thus other LEDs apart from the central LEDs in each line pattern are illuminated twice during one sequence. For example, referring to FIG. 2, let us take the horizontal line pattern 24. As one can see from FIG. 2, there are five LEDs which are illuminated to form the original line pattern. These are shown as LEDs L1, L2, L3, L4 and L5 in FIG. 2. This pattern is produced when switch SA is set to the 0 degree position and the corresponding LEDs are shown on the diagram of FIG. 2. The pattern moves from the left to the right and back from the right to the left. In this manner, the OR gates as 70 receive a first pulse during one direction from the shift register 65 and a second pulse during the next direction from shift register 65.

Thus the display traverses from L1, L2 to L5 and then back from L5 to L4 to L1 as controlled by the OR gates. In any event, transistor 91 which operates to illuminate the center LED 22 for all cases does not require an OR gate. The reason for the other OR gates is that shift register 65 may comprise more then one shift register in cascade and hence the outputs from separate shift registers are coupled together via the gates as 70 to 75.

Also shown in FIG. 4 is a circuit which consists of transistors 100 to 101. This circuit operates to select a red or green mode of operation for the LEDs shown. Essentially, LEDs are available whereby a single package contains two LEDs which will produce a red or green color depending upon the bias. The circuit consisting of transistors 100 and 101 operates to activate the display so that a red or a green illumination pattern is afforded depending upon whether transistor 100 or 101 is activated.

Figure 5:
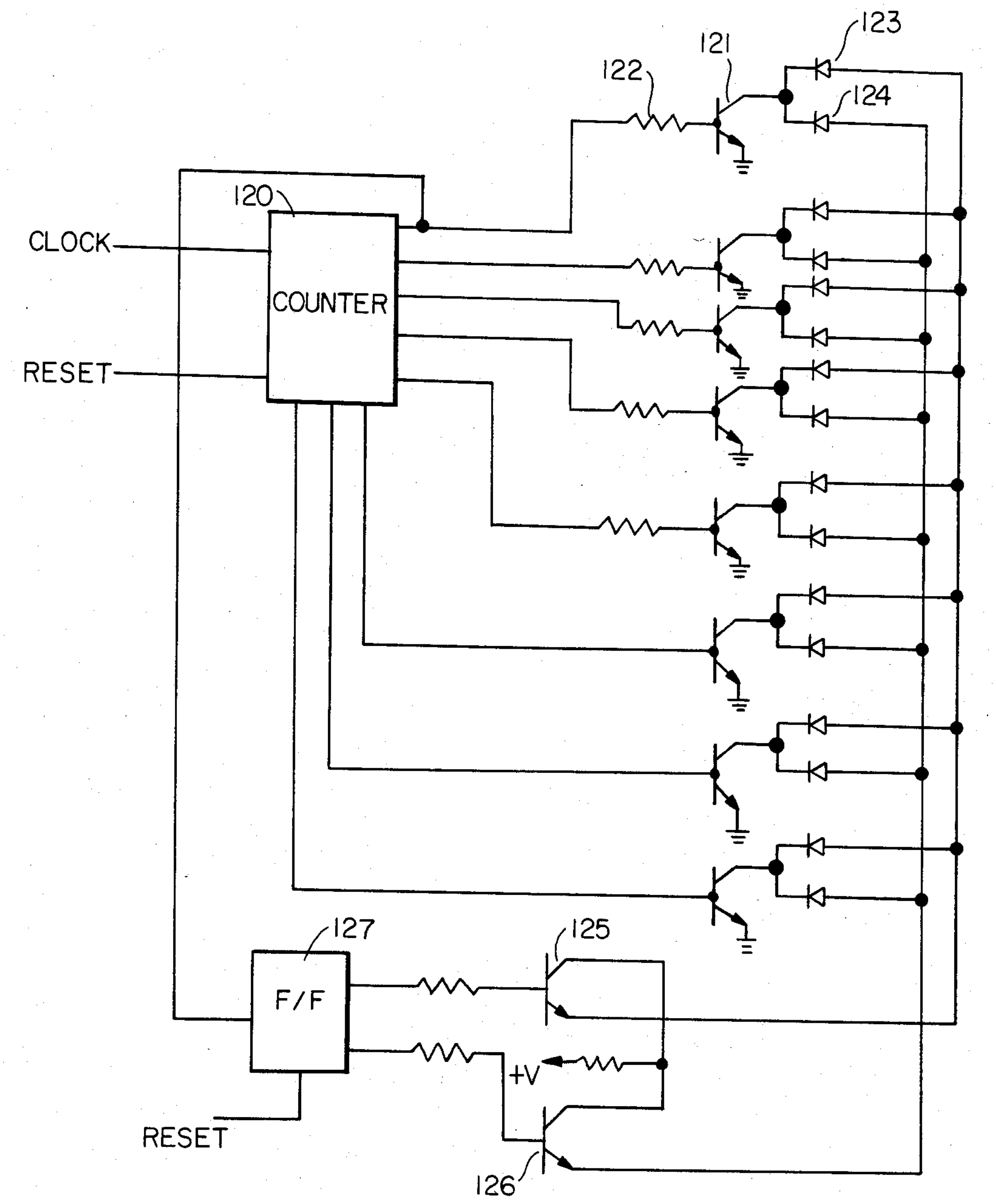
FIG. 5 is a circuit diagram showing the circuitry necessary to provide circular patterns.

Referring to FIG. 5, there is shown the necessary circuitry to produce the circular patterns manifested by circles 20 and 21 of FIG. 2. Each circular pattern contains LED devices such as devices L10 and L11 for circle 21 and L12 and L13 for circle 20.

Referring back to FIG. 5 there is shown a counter 120 which receives the clock input from inverter 55 of FIG. 4. The counter is an eight state counter where each state is decoded and is applied to the base electrode of separate transistors as transistor 121 via a current limiting resistor 122. The collector of transistor 121 is coupled to the anodes of two LED devices as 123 and 124 which essentially are positioned to form the circles 20 and 21. Thus the outputs from the counter 120 will go high in sequence then activate each LED in sequence to provide the large diameter circular display 21 on the small diameter circular display 20.

Coupled to the output of the counter is a flip flop 127 which has one output coupled to the base of transistor 125 and another output coupled to the base of transistor 126. The flip flop 127 acts as a toggle. Hence each time a sequence is implemented by the counter 120, the flip flop 127 operates, thus changing the pattern from circle 20 to circle 21. Hence in the circular mode, the outer circle for example circle 21 is first energized. At the end of this sequence, the flip flop 127 operates and the inner circle 20 is then activated. At the end of this sequence, the flip flop 127 again is operated thus permitting the outer circle to be illuminated. This alternate operation is necessary to enable the visually handicapped in improving perception while exercising eye muscle control. All components shown in regard to the above noted Figures and in particular FIGS. 3, 4 and 5 are available integrated circuit components. The transistors employed are 2N2222 devices, while the counters are designated as 4022 integrated circuits with the flip flop being a 4027 device. Such devices are conventionally available as integrated circuits. The shift registers are 4015 devices with the OR gates being 4071 devices and with the AND gates being 4011 devices. These are conventional integrated circuits available through many manufacturers and may be TTL devices or other well known integrated circuits.

Essentially, the enhancer operates to provide a user with the ability to select horizontal, vertical, oblique and circular patterns for a given period as determined by the timer of FIG. 3. These time periods can be changed and typical examples constitute ten seconds, twenty seconds, or any other suitable periods for training the visually handicapped. The enhancer thereby allows a user to be trained in rapid eye scanning in all required directions. By varying the clock, his improvement can be monitored by the practitioner.

As can be seen from the above, the use of integrated circuits allows the unit to perform all functions in an extremely reliable manner while making maintenance and construction of the unit economical and relatively inexpensive.

I claim:

1. A saccadic enhancer apparatus for training a user to develop accurate saccadic fixation in a plurality of directions comprising:

a display panel having positioned thereon a plurality of light emitting devices, a first grouping of said plurality of devices arranged in a first circular pattern of a given diameter, a second grouping of said plurality of devices arranged in a second circular pattern concentric with said first and of a smaller diameter, a third grouping of said plurality of devices arranged in a horizontal line pattern along the common horizontal diameter of said circles, a fourth grouping of said plurality of devices arranged in a vertical line pattern along the common vertical diameter of said circles, and at least a fifth grouping of said plurality of devices arranged along an oblique diameter of said circles;

a clock generator for generating a clock signal having a given repetition rate;

first selectable logic means including a counter responsive to said clock signal for providing a plurality of outputs in sequence each output indicative of an activation time for each of said devices in said first and second grouping of said plurality of devices to cause said devices to display said circular patterns when said first logic means is selected, said first logic means including switching means for enabling each of said devices in said first and second groupings in an alternating manner, said first logic means and said switching means cooperating when said first logic means is selected to cause each device in one of said first and second groupings of said plurality of devices to be energized in sequence and at the completion of said sequence to cause each device in another of said first and second groupings of said plurality of devices to be energized in sequence whereby when said first logic means is selected each light emitting device in one of said first and second circular patterns is sequentially illuminated and upon completion of said sequence each light emitting device in another of said first and second circular patterns is sequentially illuminated;

second selectable logic means including a shift register responsive to said clock signal and having a plurality of outputs each indicative of a selected one of said devices in said third, fourth, and fifth groupings of said plurality of devices, selection means coupled to said third, fourth and fifth groupings of said plurality of devices for selecting one grouping of those devices indicative of one of said line patterns, said shift register outputs and said selector means cooperating to sequentially energize those devices in a selected one of said third, fourth and fifth groupings in a sequence wherein the devices in a selected one of said third, fourth and fifth groupings are energized in an ascending order and thereafter energized in a descending order;

main selection means for selecting said first or second logic means to cause said display to provide linear or circular patterns, and selectable timing means capable of providing a plurality of selected time intervals and coupled to said first and second logic means to cause said means to provide said associated display during a selected timing interval.

2. The saccadic enhancer according to claim 1, wherein said timing means includes a low frequency clock generator, counting means coupled to said generator for providing a series of timing intervals at outputs and switching means for selecting one of said outputs indicative of said timing interval.

3. The saccadic enhancer according to claim 1, wherein said fifth grouping of said plurality of devices is arranged at an angle of 45 degrees with respect to said horizontal diameter.

4. The saccadic enhancer according to claim 1, wherein said fifth grouping of said plurality of devices is arranged at an angle of 135 degrees with respect to said horizontal diameter.

5. The saccadic enhancer according to claim 1, wherein said switching means for enabling each of said devices in said first and second groupings in an alternating manner includes a toggle flip flop having an input coupled to said counter with a first output coupled to said first grouping of said plurality of devices and a second output coupled to said second grouping of said plurality of devices.

6. The saccadic enhancer according to claim 1, wherein said plurality of devices take the form of light emitting diodes.

7. The saccadic enhancer according to claim 6, further including illumination control means coupled to said diodes for selecting a first illumination color in a first state and a second illumination color in a second state.

8. The saccadic enhancer according to claim 7, wherein said first color is red and said second color is green.

9. The saccadic enhancer according to claim 1, wherein said clock generator includes means for selectively varying the repetition rate to therefore vary the sequential rate of a displayed pattern.

10. The saccadic enhancer according to claim 1, wherein said selectable timing means includes means for varying the duration of said timing intervals as selected.

* * * * *